(12) United States Patent
Hsin et al.

(10) Patent No.: US 10,448,878 B2
(45) Date of Patent: Oct. 22, 2019

(54) SYSTEM AND METHOD FOR TEMPORAL AND SPATIAL DETECTION OF SEIZURE ONSET

(71) Applicant: CHUNG SHAN MEDICAL UNIVERSITY HOSPITAL, Taichung (TW)

(72) Inventors: Yue-Loong Hsin, Taichung (TW); Syu-Jyun Peng, Taichung (TW)

(73) Assignee: CHUNG SHAN MEDICAL UNIVERSITY HOSPITAL, Taichung (TW)

( * ) Notice: Subject to any disclaimer, the term of this patent is extended or adjusted under 35 U.S.C. 154(b) by 295 days.

(21) Appl. No.: 15/489,725

(22) Filed: Apr. 17, 2017

(65) Prior Publication Data

US 2018/0098725 A1    Apr. 12, 2018

(30) Foreign Application Priority Data

Oct. 7, 2016    (TW) .................................. 105132496

(51) Int. Cl.
*A61B 5/00* (2006.01)
*A61B 5/0478* (2006.01)
(Continued)

(52) U.S. Cl.
CPC ............ *A61B 5/4094* (2013.01); *A61B 5/048* (2013.01); *A61B 5/0476* (2013.01); *A61B 5/0478* (2013.01); *A61N 1/0526* (2013.01); *A61N 1/0531* (2013.01); *A61N 1/0534* (2013.01); *A61M 5/172* (2013.01)

(58) Field of Classification Search
None
See application file for complete search history.

(56) References Cited

U.S. PATENT DOCUMENTS

2010/0292602 A1*  11/2010  Worrell ............... A61B 5/0478
                                                            600/544

OTHER PUBLICATIONS

Staba et al. Quantitative Analysis of High-Frequency Oscillations (80-500 Hz) Recorded in Human Epileptic Hippocampus and Entorhinal Cortex. Journal of Neurophysiology, vol. 88, Oct. 2002. (Year: 2002).*

(Continued)

*Primary Examiner* — Etsub D Berhanu
(74) *Attorney, Agent, or Firm* — Cheng-Ju Chiang (57) ABSTRACT

Many electrodes are positioned inside a skull for obtaining several electric voltage variation wave information. A processing unit computes subtract operation between two neighboring electrical voltage variation wave information respectively and then can obtain electrical voltage difference waves. Furthermore, each electrical voltage difference wave is separated into a first band wave signal and a second band wave signal. After which, several first band wave envelope signals and second band wave envelope signals are obtained. It conducts a co-relation processing about the first band wave envelope signals and the second band wave envelope signals. So, a co-relation table is obtained for determining a position where an intracranial brain wave abnormality occurs. In this invention, a unique scientific approach to determine the spatial position of seizure onset occurred inside the brain. In addition, the position of intracranial brain wave abnormality can be concretized and visualized by the co-relation table.

6 Claims, 10 Drawing Sheets

(51) Int. Cl.
*A61B 5/0476* (2006.01)
*A61B 5/048* (2006.01)
*A61N 1/05* (2006.01)
*A61M 5/172* (2006.01)

(56) References Cited

OTHER PUBLICATIONS

Bragin et al. High-Frequency Oscillations in Human Brain. Hippocampus 9:137-142 (1999). (Year: 1999).*
Engel, Jr. et al. High-frequency oscillations: What is normal and what is not? Epilepsia, 50(4):598-604, 2009. (Year: 2009).*
Staba et al. Increased Fast Ripple to Ripple Ratios Correlate with Reduced Hippocampal Volumes and Neuron Loss in Temporal Lobe Epilepsy Patients. Epilepsia, 48(11):2130-2138, 2007. (Year: 2007).*
Garcia-Barba et al. The Brain Topology of Fast Ripples, and their Correlation with Epilepsy. Journal of Neurological Disorders, 2014, 2:4. (Year: 2014).*

* cited by examiner

SYSTEM AND METHOD FOR TEMPORAL AND SPATIAL DETECTION OF SEIZURE ONSET

BACKGROUND OF THE INVENTION

1. Field of Invention

This invention relates to a system and method for temporal and spatial detection of seizure onset. Particularly, it relates to a system and method for temporal and spatial detection of seizure onset that utilizes a unique scientific approach to determine the spatial position of seizure onset occurred inside the brain. In addition, the position of intracranial brain wave abnormality can be concretized and visualized by the co-relation table.

2. Description of the Prior Art

There many kinds of diseases about intracranial brain wave abnormalities. The most typical one is called epilepsy. Of course, it could be other brain damage or diseases. Basically, epilepsy is caused by overactive brain neurons. It is just like an unpredictable wire fire without warning. One or more electricity discharges suddenly happen in one or more zones where such electricity discharges should not occur. As a result, it makes the electrical level and distribution inside the brain becomes messy.

In the past, a traditional brain wave detection only can detect the electricity variation at one or more specific points outside the skull. Based on these information, an experienced medical doctor can roughly determine or tried to predict the reason of such brain waves abnormalities. However, the traditional way still has the following disadvantages. First, it is quite difficult to precisely predict the exact spatial position of the abnormal electricity discharges happened inside the skull. Also, it is hard to use a more scientific approach to find out the precise happening position(s) of intracranial brain wave abnormalities.

SUMMARY OF THE INVENTION

The object of this invention is to provide a system and method for temporal and spatial detection of seizure onset. Not only it utilizes a unique approach to determine the spatial position of seizure onset occurred inside the brain, but also the position of intracranial brain wave abnormality can be concretized and visualized by the co-relation table. Therefore, this invention can solve the traditional problems as follows. The traditional way is quite difficult to predict the exact spatial position of the abnormal electricity discharges happened inside the skull. Also, the traditional way is hard to use a more scientific approach to find out the precise happening position(s) of intracranial brain wave abnormalities.

In order to solve the above-mentioned traditional problems, this invention is provided as a technical solution.

A system for temporal and spatial detection of seizure onset comprising:

an electrode unit for positioning inside or on an outer surface of a brain portion, the electrode unit including at least one electrode collection sub-unit, each electrode collection sub-unit containing a plurality of electrodes for corresponding a plurality of detection points, the quantity of the electrodes being defined as M, the quantity of detection points being defined as M as well; and a processing unit being electrically connected to the electrode unit and including an original electrical voltage collecting module, an electrical voltage difference processing module, a frequency separating processing module, an electrical voltage wave envelope processing module, and a co-relation processing module;

the original electrical voltage collecting module being configured to detect the detection points via the electrodes for a working time so as to obtain a plurality of electric voltage variation wave information; wherein the quantity of M being a positive integer and being greater than or equal to 4;

the electrical voltage difference processing module which connects with the original electrical voltage collecting module being configured to get all the electric voltage variation wave information having the quantity of M and then to compute a subtract operation between two neighboring electrical voltage variation wave information respectively, finally a plurality of electrical voltage difference waves having the quantity of M−1 being obtained;

the frequency separating processing module which connects with the electrical voltage difference processing module be configured to conduct a frequency separating process for every electrical voltage difference wave, so that each electrical voltage difference wave being filtered out and separated into a first band wave signal and a second band wave signal, in which the first band wave signal having a frequency range of 80-250Hz, the second band wave signal having a frequency range of 250-600 Hz;

the electrical voltage wave envelope processing module which connects with the frequency separating processing module adapted to get a plurality of wave envelope lines of the first band wave signals so as to obtain several first band wave envelope signals and to get a plurality of wave envelope lines of the second band wave signals so as to obtain several second band wave envelope signals; and the co-relation processing module which connects with the electrical voltage wave envelope processing module being configured to conduct a co-relation processing during a time segment of the working time and said co-relation processing being performed between respective first band wave envelope signals and second band wave envelope signals, so that a co-relation table in a two-dimensional (M−1) by (M−1) form, so as to determine a position where an intracranial brain wave abnormality occurs.

About the method for temporal and spatial detection of seizure onset, it comprises the steps of:
(1) original electrical voltage collecting step;
(2) electrical voltage difference processing step;
(3) frequency separating processing step;
(4) electrical voltage wave envelope processing step; and
(5) co-relation processing step.

DESCRIPTION OD THE PREFERRED EMBODIMENT

Figure 1A:
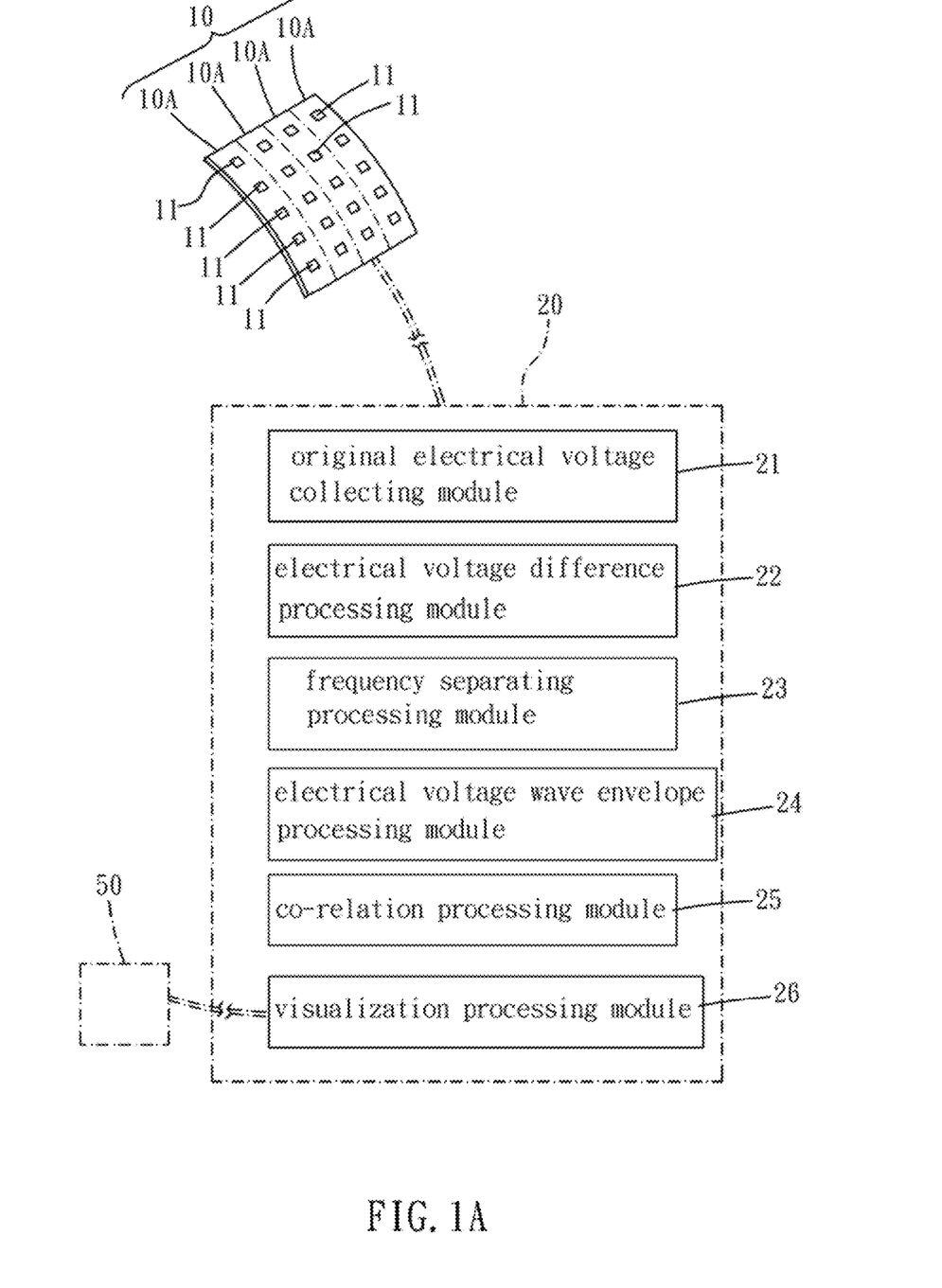
FIG. 1A is a perspective view of this invention.
Figure 2:
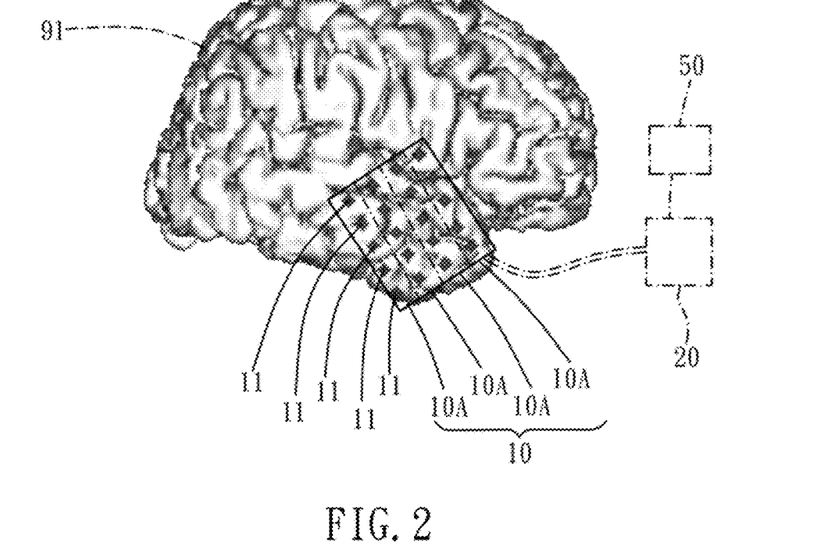
FIG. 2 is an illustration of an application in the brain portion of this invention.

This invention relates to a system and method for temporal and spatial detection of seizure onset. As shown in FIGS. 1A and 2, the system includes an electrode unit 10 and a processing unit 20.

With regard to this electrode unit 10, the electrode unit 10 is provided for positioning inside a brain portion 91 of a user. The electrode unit 10 includes at least one electrode collection sub-unit 10A. Each electrode collection sub-unit 10A contains a plurality of electrodes 11 for corresponding a plurality of detection points of the brain portion 91. The quantity of the electrodes 11 is defined as M. The quantity of detection points is defined as M as well.

Concerning the processing unit 20, it is electrically connected to the electrode unit 10 and includes an original electrical voltage collecting module 21, an electrical voltage difference processing module 22, a frequency separating processing module 23, an electrical voltage wave envelope processing module 24, and a co-relation processing module 25.

Figure 8:
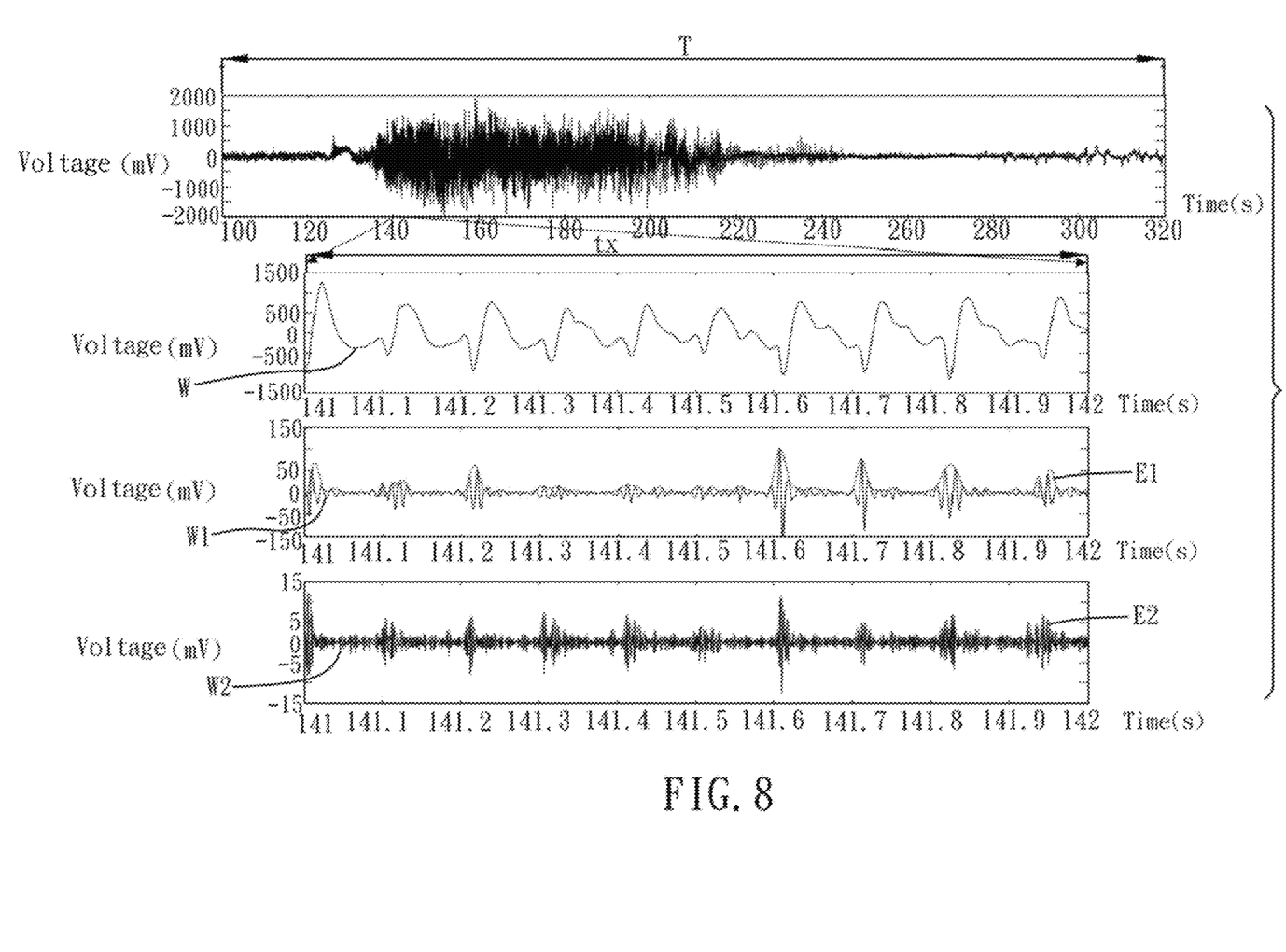
FIG. 8 shows one of the electrical voltage difference waves, a first band wave signal and a second band wave signal.

The original electrical voltage collecting module 21 is able to detect these detection points via the electrodes 11 for a working time T so as to obtain a plurality of electric voltage variation wave information (as shown in FIG. 8, all the electric voltage variation wave information can be obtained within the working time T). Furthermore, the quantity of M is a positive integer and is greater than or equal to 4.

The electrical voltage difference processing module 22 which connects with the original electrical voltage collecting module 21 is able to get all the electric voltage variation wave information having the quantity of M and then to compute a subtract operation between two neighboring electrical voltage variation wave information respectively. Finally, a plurality of electrical voltage difference waves W (as show in FIG. 7) having the quantity of M−1 can be obtained.

The frequency separating processing module 23 which connects with the electrical voltage difference processing module 22 is able to conduct a frequency separating process so that a first band wave signal W1 and a second band wave signal W2 are filtered out and obtained (as illustrated in FIG. 8). The first band wave signal W1 has frequency range of 80-250 Hz. The second band wave signal W2 having a frequency range of 250-600 Hz.

Figure 9:
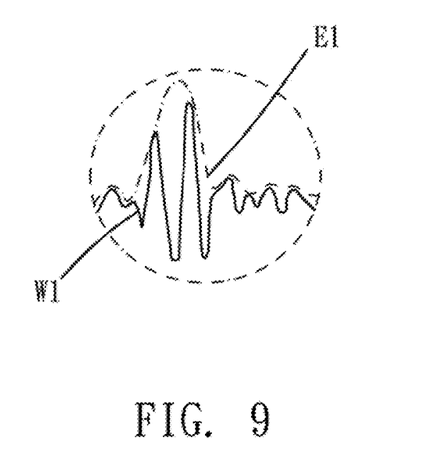
FIG. 9 is a view showing a portion of one of the first band wave envelope signal.
Figure 10:
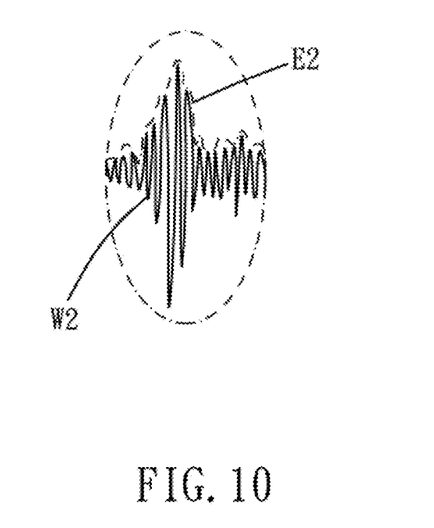
FIG. 10 is a view showing a portion of the second band wave envelope signal.

Concerning the electrical voltage wave envelope processing module 24, it connects with the frequency separating processing module 23 and it can get a plurality of wave envelope lines of the first band wave signals W1 so as to obtain several first band wave envelope signals E1 (as illustrated in FIG. 9) having the quantity of M−1. Similarly, the electrical voltage wave envelope processing module 24 can get a plurality of wave envelope lines of the second band wave signals W2 as well, so that several second band wave envelope signals E2 (as shown in FIG. 10) having the quantity of M−1 can be obtained.

Figure 11:
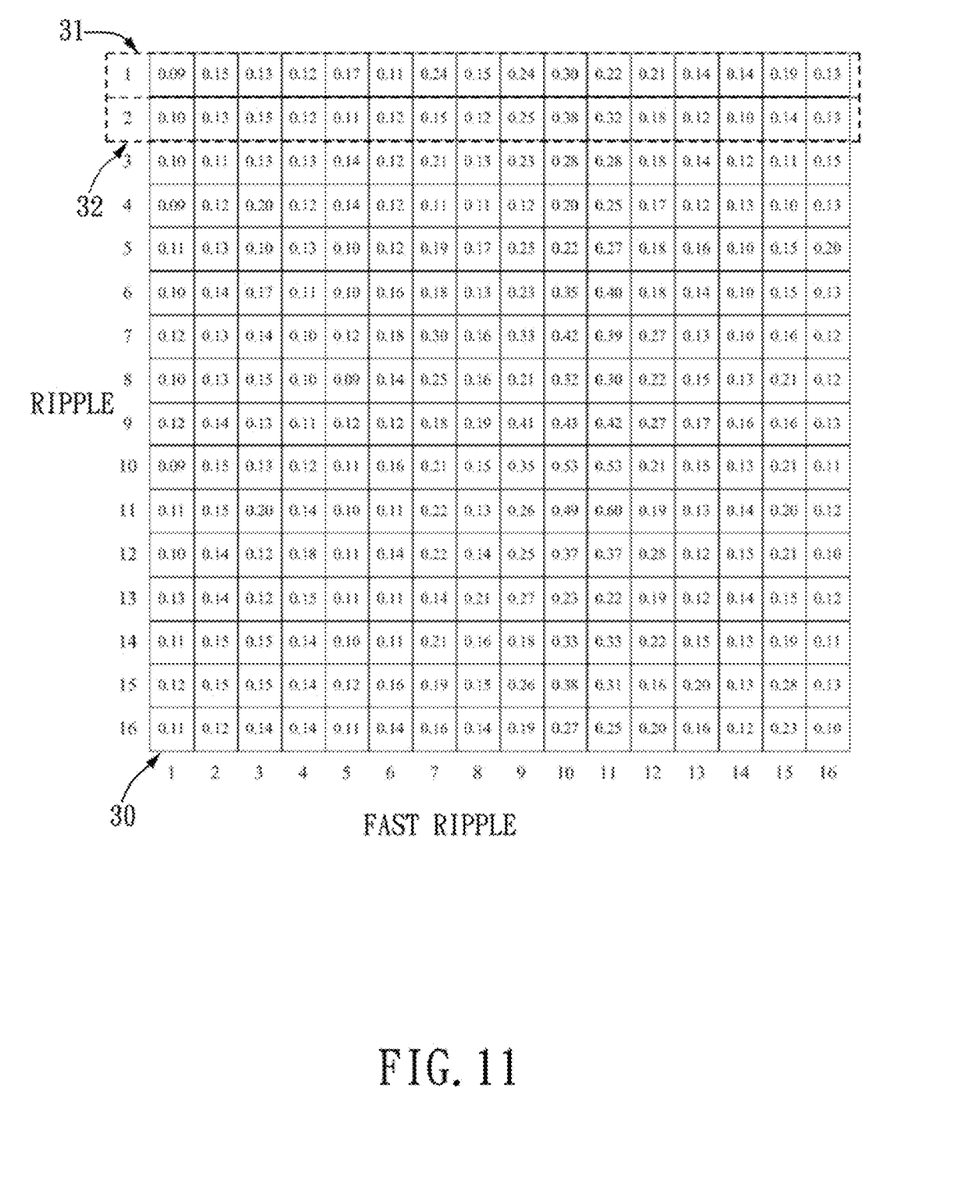
FIG. 11 shows the co-relation table in the first practical application.

About the co-relation processing module 25 which connects with the electrical voltage wave envelope processing module 24 is able to conduct a co-relation processing during a time segment tx of the working time T about the first band wave envelope signals E1 and the second band wave envelope signals E2. So, a co-relation table 30 (as shown in FIG. 11) in a two-dimensional (M−1) by (M−1) form can be obtained. Hence, it can be used to determine a position where an intracranial brain wave abnormality occurs.

In an actual application, the structure of this electrode unit 10 can be formed as an elongated thin film, a rectangular thin film (such as a 2-D thin film), a needle structure, or their combination.

When it is an elongated thin film (can be seen in FIG. 5), these electrodes 11 having the quantity (or quantity) of M are aligned. The electrode unit 10 is placed on an outer surface of a brain portion (not shown in FIG. 5).

Figure 3:
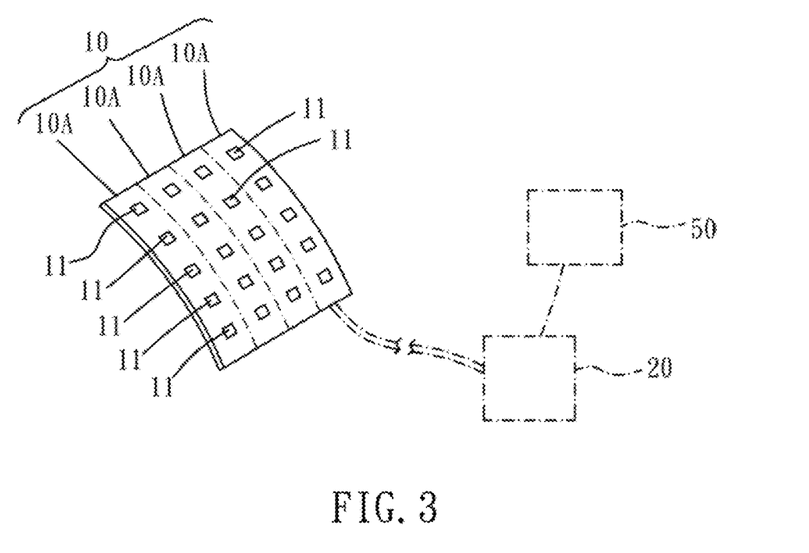
FIG. 3 is a view showing electrode unit, the processing unit, and the display of this invention.
Figure 4:
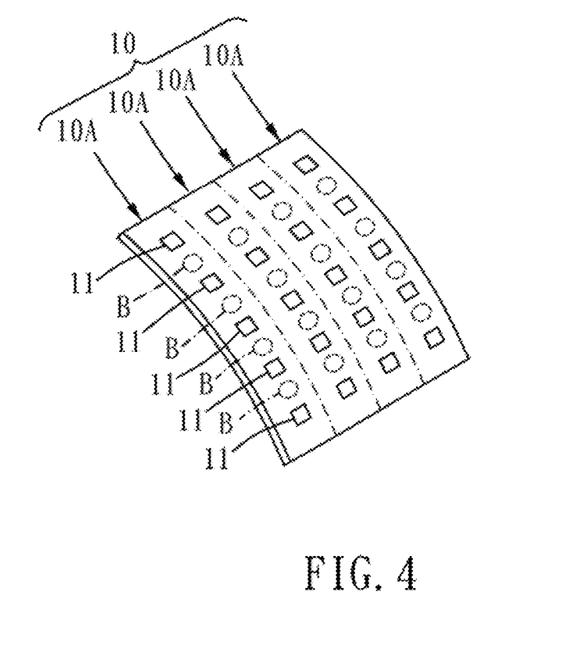
FIG. 4 is a view showing the middle zone of the electrode unit.

When it is a rectangular thin film (as depicted in FIGS. 3 and 4), the electrode units 10 contains several rows of electrode collection sub-units 10A and the quantity of rows being defined as N. They are parallel and connected each other. And, the quantity of N (a positive integer) is greater than or equal to three so that the two-dimensional rectangular thin film has at least 4 ×3 electrodes. Hence, a 2-D square or rectangular thin film is formed for covering larger area.

Figures 5, 6:
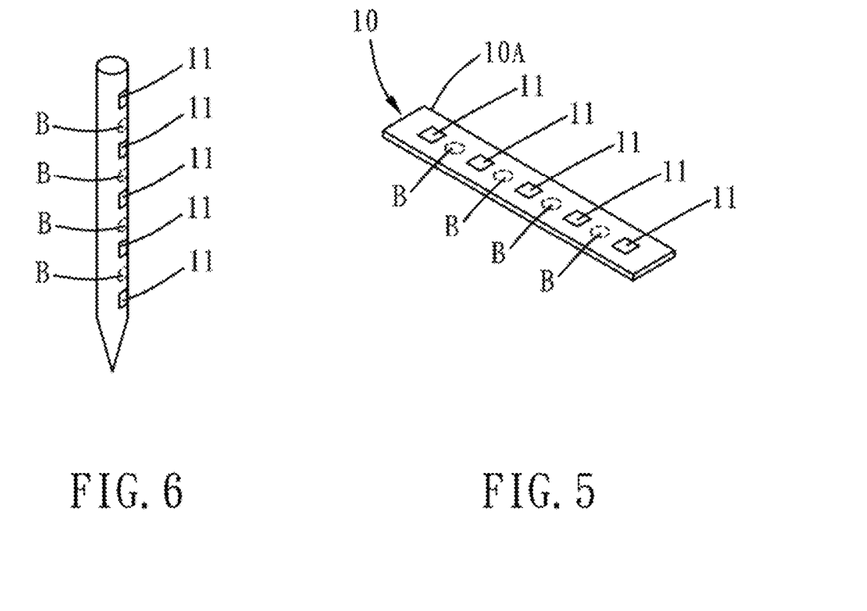
FIG. 5 is a view showing an embodiment about the rectangular thin film of the electrode unit.
FIG. 6 is a view showing another embodiment about the needle structure of the electrode unit.

If the electrode unit 10 is shaped as a needle structure as illustrated in FIG. 6, it can be inserted into the brain portion 91 easier.

Referring to FIGS. 2, 3, and 4, for example, the quantity of electrode collection sub-units 10A could be four. Each electrode collection sub-unit 10A could have five electrodes 11. Therefore, there will be total 20 electrodes 11 (because 4×5=20).

Figure 7:
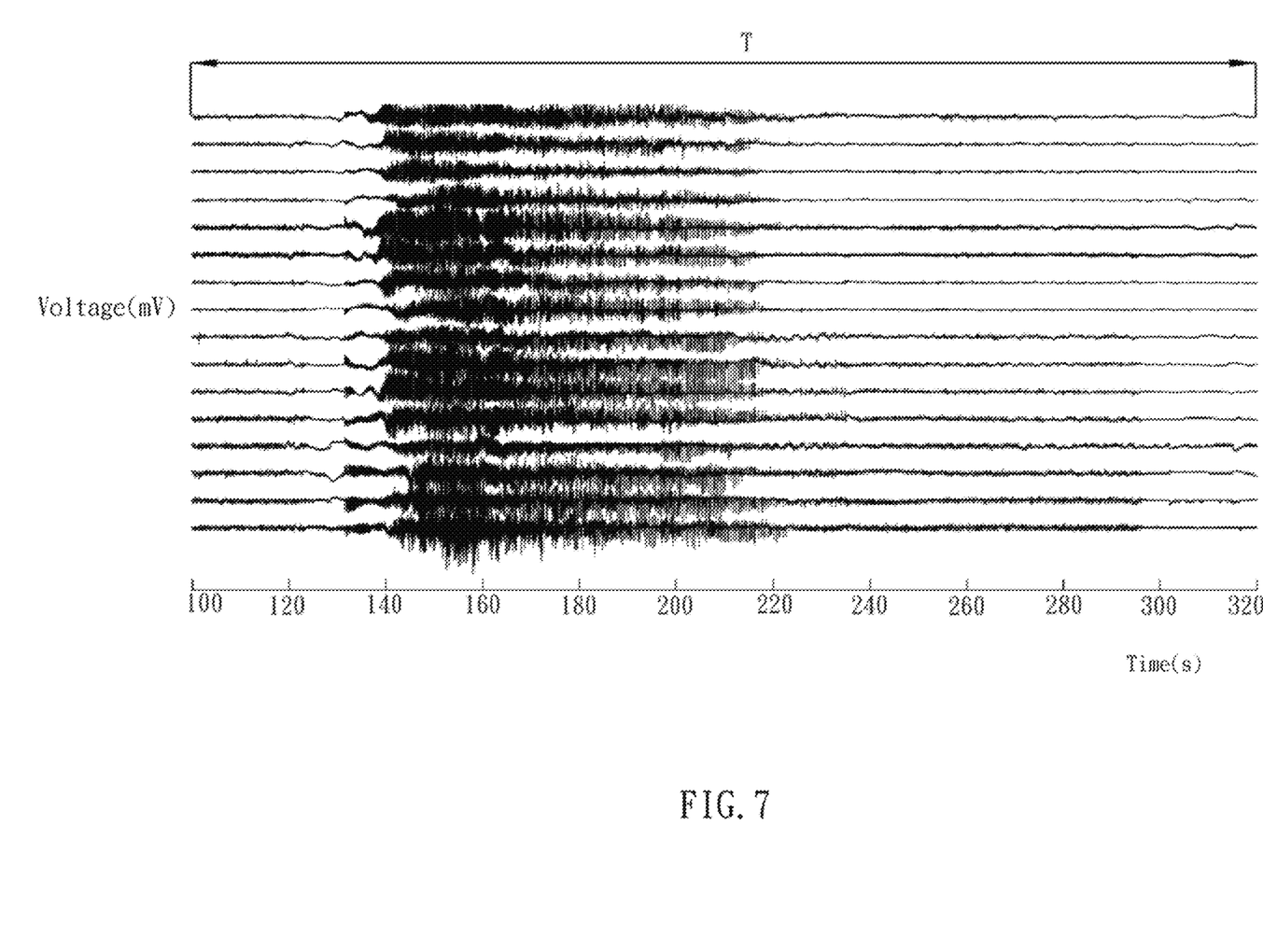
FIG. 7 shows a plurality of electrical voltage difference waves.

For each electrode collection sub-unit 10A, there is a middle zone B between the first and the second electrodes 11. There is another middle zone B between the second and the third electrodes 11. Also, there is one between the third and the fourth electrodes 11. Plus, there is another one between the fourth and the fifth electrodes 11. Thus, every two neighboring electrodes 11 contain a middle zone B (as shown in FIGS. 5 and 6). Every middle zone B is corresponding to a specific electrical voltage difference wave W which is measured by two neighboring electrodes. In this example, there are total four electrode collection sub-units 10A, so (5-1) ×4=4×4=16. Hence, 16 electrical voltage difference waves W can be obtained, as illustrated in FIG. 7. In which, the X-axis means time with the unit of second (the working time T is selected between the 100th second to the 300th second as an example). The Y-axis means the voltage with the unit of mV. In this example, there are total 16 electrical voltage difference waves W. A sampling rate is preferably at least 4kHz.

Of course, if one utilizes the second preferred embodiment shown in FIG. 5. It is an elongated thin film. There is only one electrode collection sub-unit 10A. It contains 4 electrodes 11. Because (4−1)×1=3, there are 3 electrical voltage difference waves W.

Similarly, if the shape is changed to the third preferred embodiment as illustrated in FIG. 6 (like a needle structure which is inserted into the brain portion 91), there is only one electrode collection sub-unit 10A. However, it contains 5 electrodes 11. Because (5−1)×1=4, total 4 electrical voltage difference waves W can be obtained.

With regard to the frequency separating processing module 23, it connects with the frequency separating processing module 23. As shown in FIG. 8, a time range from the 141th second to the 142th second is selected as an example for describing this frequency separating processing procedure. After the frequency separating processing, every electrical voltage difference wave W will be filtered out and separated into two bands, namely the first band wave signal W1 and the second band wave signal W2.

Concerning the electrical voltage wave envelope processing module 24, it connects with the frequency separating processing module 23 and it can obtain several first band wave envelope signals E1 from the first band wave signals W1 and obtain several second band wave envelope signals E2 from the second band wave signals W2. Please refer to FIG. 8 (specifically referring to the two lower blocks or tracks in FIG. 8), FIG. 9, and FIG. 10. The technique about getting a wave envelope line of an electrical wave signals is a prior art or a well-known technology (so no detail is needed here). Generally, this technique may be called ENVELOPE (or ENVOLOPE WAVE) which is widely used in electrical wave processing or acoustic waves processing fields. The term ENVELOPE in this invention means to enclose the approximate outer shape outline of a wave, rather than means the data envelope technique which is used in data transmission field.

About the co-relation processing module 25, it connects with the electrical voltage wave envelope processing module 24 and can get first band wave envelope signals E1 and the second band wave envelope signals E2. In this preferred embodiment, there are 16 first band wave envelope signals E1 and another 16 second band wave envelope signals E2.

Because the first band is ranged of 80-250 Hz, it means Ripple in Brain Science. It also means degree of the nerve cell generates a yielding (or called stopping) signal. The second band is ranged of 250-600 Hz, it means Fast Ripple in Brain Science. It also means degree of the nerve cell generates an exciting signal.

Then, the autocorrelation degree computation is applied. This co-relation processing is a prior art and is widely-used in mathematic science (so no details are needed here). First of all, one should pick the first one of the 16 first band wave envelope signals E1 as a base, and then to conduct a co-relation processing with all these 16 second band wave envelope signals E2, so that 16 results will be obtained. As illustrated in the zone 31 of the co-relation table 30 in FIG. 11, the results are 0.09, 0.15, 0.13, 0.12, 0.17, . . . (omitted).

After which, one can pick the second of the 16 first band wave envelope signals E1 as a base, and then to conduct a co-relation processing with all these 16 second band wave envelope signals E2, so that another 16 results will be obtained. As illustrated in the zone 32 of the co-relation table 30 in FIG. 11, the results are 0.10, 0.13, 0.15, 0.12, 0.11, . . . (omitted).

By repeating the above procedures, 16×16 results can be obtained eventually. That forms the co-relation table 30. Of course, it can be shown on a display 50 (or a monitor).

Figure 13:
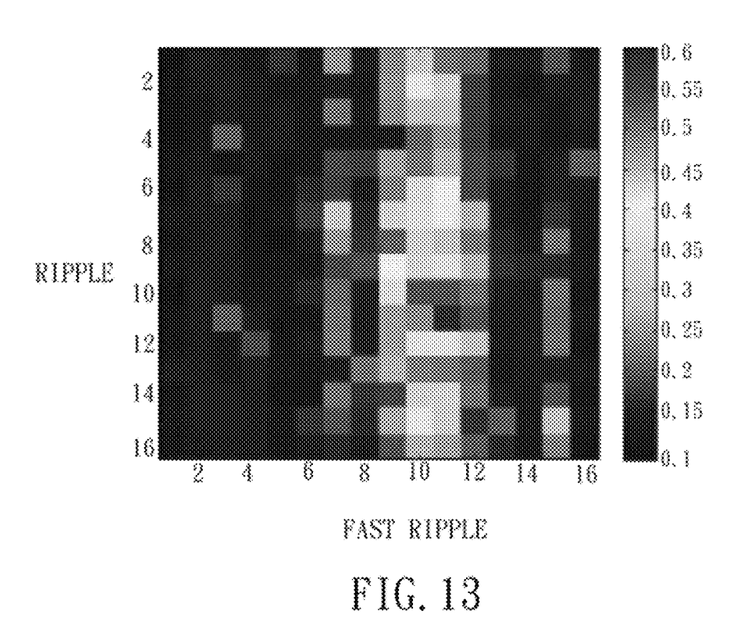
FIG. 13 shows the visualized condition (shown in grey scales) of the co-relation table in FIG. 11.
Figure 14:
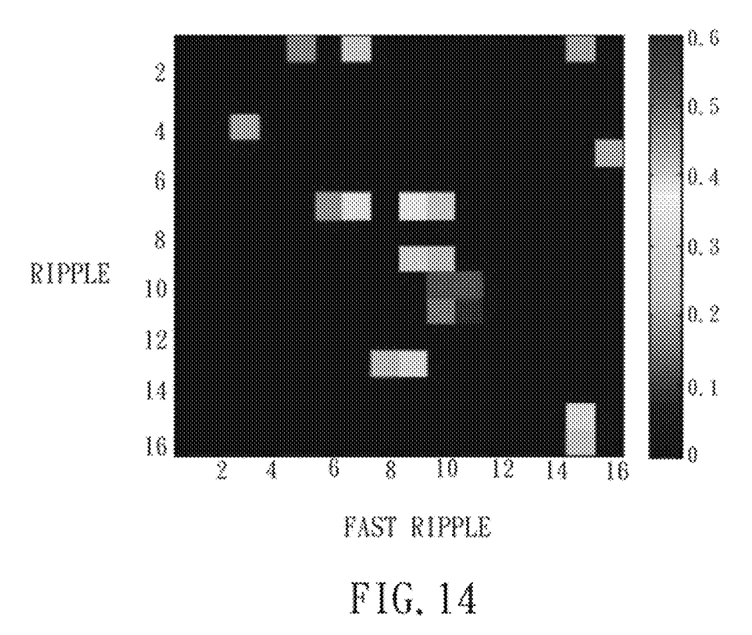
FIG. 14 shows the visualized condition (shown in grey scales) of the co-relation table in FIG. 12.

Of course, if the result is below a preset relatively low value, it can be replaced by zero. But, the relatively high value still be kept for showing up. For example, the data in the zone 41 of the co-relation table 40 in FIG. 12 becomes 0, 0, 0, 0, 0.17, . . . (omitted). The data in the zone 42 of co-relation table 40 in FIG. 12 becomes 0, 0, 0, 0, 0, . . . (omitted). Hence, only the points with higher co-relation portions will be shown, since they mean the possible points (or zones) where an intracranial brain wave abnormality occurs The processing unit 20 may further include a visualization processing module 26. The visualization processing module 26 connects with the co-relation processing module 25 and can process the values in the (M−1)×(M−1) co-relation table 30,40 by converting into predetermined colors or grey scales. So, it becomes a (M−1)×(M−1) colored (or grey scaled) blocks in the co-relation table 30,40 for better visualization effect. As shown in FIG. 13, it shows the visualized results of the co-relation table 30,40 shown in FIG. 11 after processed. It can be shown on a display 50. Also, as illustrated in FIG. 14, it is another co-relation table 30,40 shown in FIG. 12 after processed and the be illustrated in a display 50.

Figure 1B:
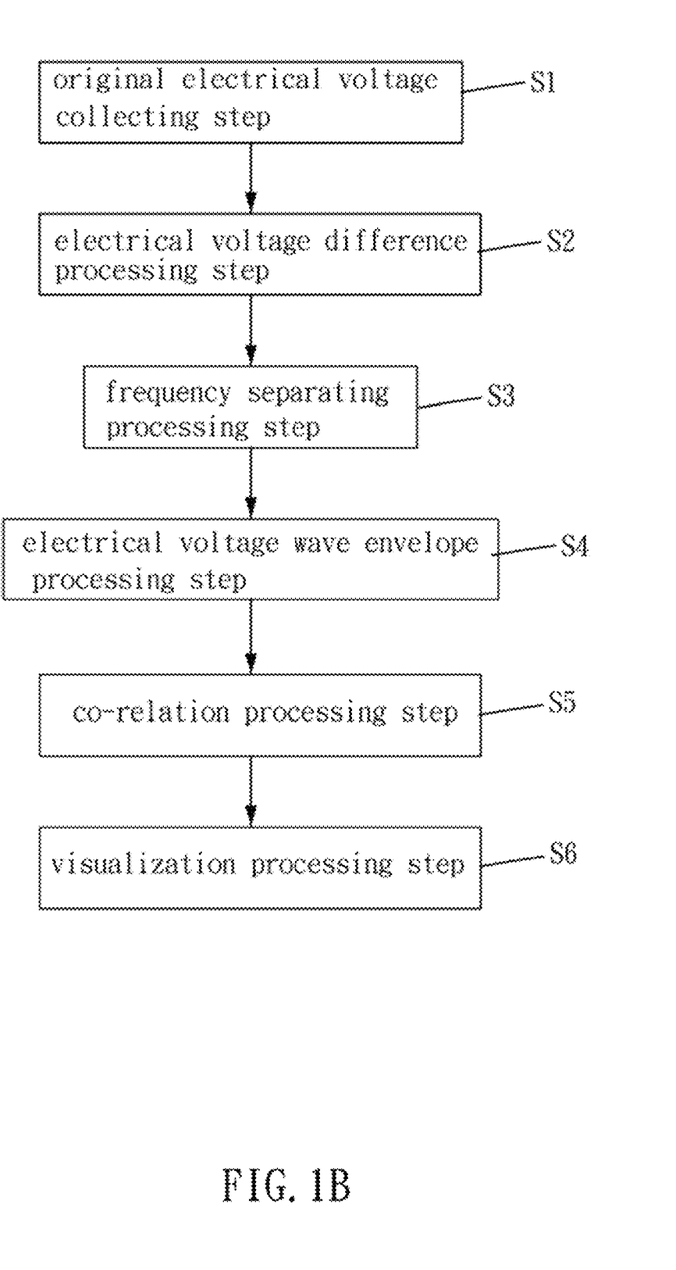
FIG. 1B is a flow chart of this invention.

Referring to FIGS. 1A, 1B, and 2, the method for temporal and spatial detection of seizure onset of this invention mainly comprises the following steps, namely (1) original electrical voltage collecting step S1, (2) electrical voltage difference processing step S2, (3) frequency separating processing step S3, (4) electrical voltage wave envelope processing step S4, and (5) co-relation processing step S5.

Concerning this original electrical voltage collecting step S1, it is to provide an electrode unit 10 for positioning inside a brain portion 91. The electrode unit 10 includes at least one electrode collection sub-unit 10A. Each electrode collection sub-unit 10A contains a plurality of electrodes 11 for corresponding a plurality of detection points. The quantity of the electrodes 11 is defined as M. The quantity of detection points is defined as M as well. This electrode unit 10 can detect the detection points via the electrodes 11 for a working time so as to obtain a plurality of electric voltage variation wave information. In which, the quantity of M is a positive integer and being greater than or equal to 4.

About the electrical voltage difference processing step S2, it is to provide a processing unit 20 that is electrically connected to the electrode unit 10 for getting all the electric voltage variation wave information having the quantity of M and then computing subtract operation between two neighboring electrical voltage variation wave information respectively. Finally, a plurality of electrical voltage difference waves W having the quantity of M−1 can be obtained.

With regard to the frequency separating processing step S3, this processing unit 20 conducts a frequency separating process for every electrical voltage difference wave W, so that each electrical voltage difference wave W is filtered out and separated into a first band wave signal W1 and a second band wave signal W2. In which, the first band wave signal W1 has a frequency range of 80-250 Hz, and the second band wave signal W2 has a frequency range of 250-600 Hz.

Regarding the electrical voltage wave envelope processing step S4, the processing unit gets a plurality of wave envelope lines of the first band wave signals W1 so as to obtain several first band wave envelope signals E1 and gets a plurality of wave envelope lines of the second band wave signals W2 so as to obtain several second band wave envelope signals E2.

Concerning the co-relation processing step S5, the processing unit 20 conducts a co-relation processing during a time segment tx of the working time T about the first band wave envelope signals E1 and the second band wave envelope signals E2. Thus, a (M−1)×(M−1) co-relation table 30 (as shown in FIG. 11) can be obtained for determining a position where an intracranial brain wave abnormality occurs.

In an actual application of the original electrical voltage collecting step S1, this electrode unit 10 can be a structure formed as an elongated thin film, a rectangular thin film (such as a 2-D thin film), a needle structure, or their combination.

When it is an elongated thin film (can be seen in FIG. 5), these electrodes 11 having the quantity of M are aligned. The electrode unit 10 is placed on an outer surface of a brain portion (not shown in FIG. 5).

When it is a rectangular thin film (as depicted in FIGS. 3 and 4), the electrode units 10 contains several electrode collection sub-units 10A (having the quantity of N). They are parallel and connected each other. And, the quantity of N is greater than or equal to three. Hence, a square or rectangular thin film is formed for covering larger area.

If the electrode unit 10 is shaped as a needle structure as illustrated in FIG. 6, it can be inserted into the brain portion 91 easier.

Referring to FIGS. 2, 3, and 4, for example, the quantity of electrode collection sub-units 10A could be four. Each electrode collection sub-unit 10A could have five electrodes 11. Therefore, there will be total 20 electrodes 11 (because 4×5=20).

In the electrical voltage difference processing step S2, about each electrode collection sub-unit 10A, there is a middle zone B between the first and the second electrodes 11. There is another middle zone B between the second and the third electrodes 11 Also, there is one between the third and the fourth electrodes 11 as well as another one between the fourth and the fifth electrodes 11. Thus, every two neighboring electrodes 11 contain a middle zone B (as shown in FIGS. 5 and 6). Every middle zone B is corresponding to a specific electrical voltage difference wave W. There are total four electrode collection sub-unit 10A, so (5−1)×4=4×4=16. Hence, 16 electrical voltage difference waves W can be obtained, as illustrated in FIG. 7. In which, the X-axis means time with the unit of second (the working time T is selected between the 100th second to the 300th second as an example). The Y-axis means the voltage with the unit of mV. In this example, there are total 16 electrical voltage difference waves W. In which, a sampling rate is preferably at least 4 kHz.

Of course, if one utilizes the second preferred embodiment shown in FIG. 5. It is an elongated thin film. There is only one electrode collection sub-unit 10A. It contains 4 electrodes 11. Because (4−1)×1=3, there are 3 electrical voltage difference waves W.

Similarly, if the shape is changed to the third preferred embodiment as illustrated in FIG. 6 (like a needle structure which is inserted into the brain portion 91), there is only one electrode collection sub-unit 10A. However, it contains 5 electrodes 11. Because (5−1)×1=4, total 4 electrical voltage difference waves W can be obtained.

With regard to the frequency separating processing step S3, as shown in FIG. 8, a time range from the 141th second to the 142th second is selected as an example for describing this frequency separating processing procedure. After the frequency separating processing, every electrical voltage difference wave W will be filtered out and separated into two bands, namely the first band wave signal W1 and the second band wave signal W2.

In the electrical voltage wave envelope processing step S4, please refer to FIG. 8 (specifically means two lower blocks or tracks in FIG. 8), FIG. 9, and FIG. 10. It can obtain several first band wave envelope signals E1 from the first band wave signals W1 and obtain several second band wave envelope signals E2 from the second band wave signals W2.

The technique about getting a wave envelope line of an electrical wave signals is a prior art or a well-known technology (so no detail is needed here). Generally, this technique may be called ENVELOPE (or ENVELOPE WAVE) which is widely used in electrical wave processing or acoustic waves processing fields. The term ENVELOPE in this invention means to enclose the approximate outer shape outline of a wave, rather than means the one used in data transmission field.

About the co-relation processing step S5, in this preferred embodiment, there are 16 first band wave envelope signals E1 and another 16 second band wave envelope signals E2.

Because the first band is ranged of 80-250 Hz, it means Ripple in Brain Science. It also means degree of the nerve cell generates a yielding (or called to stop) signal. The second band is ranged of 250-600 Hz, it means Fast Ripple in Brain Science. It also means degree of the nerve cell generates an exciting signal.

Then, the autocorrelation degree computation is applied. This co-relation processing is a prior art and is widely-used in mathematic science (so no details is needed here). First of all, one should pick the first one of the 16 first band wave envelope signals E1 as a base, and then to conduct a co-relation processing with all these 16 second band wave envelope signals E2, so that 16 results will be obtained. As illustrated in the zone 31 of the co-relation table 30 in FIG. 11, the results are 0.09, 0.15, 0.13, 0.12, 0.17, . . . (omitted).

After which, one can pick the second of the 16 first band wave envelope signals E1 as a base, and then to conduct a co-relation processing with all these 16 second band wave envelope signals E2, so that another 16 results will be obtained. As illustrated in the zone 32 of the co-relation table 30 in FIG. 11, the results are 0.10, 0.13, 0.15, 0.12, 0.11, . . . (omitted).

By repeating the above procedures, 16×16 results can be obtained eventually. That forms the co-relation table 30. Of course, it can be shown on a display 50 (or a monitor).

Of course, if the result is below a relative low value, it can be replaced by zero. But, the relatively high value still be kept for showing up. For example, the data in the zone 41 of the co-relation table 40 in FIG. 12 becomes 0, 0, 0, 0, 0.17, . . . (omitted). The data in the zone 42 of co-relation table 40 in FIG. 12 becomes 0, 0, 0, 0, 0, . . . (omitted). Hence, only the points with high co-relation portions will be shown, since they mean the possible points (or zones) where an intracranial brain wave abnormality occurs Moreover, after the co-relation processing step S5, it is optional to include a visualization processing step S6.

In this visualization processing step S6, it can process the values in the (M−1)×(M−1) co-relation table 30,40 by converting into predetermined colors (or grey scales). So, it becomes a (M−1)×(M−1) colored (or grey scaled) blocks in the co-relation table 30,40 for better visualization effect. As shown in FIG. 13, it shows the visualized results of the co-relation table 30,40 shown in FIG. 11 after processed. It can be shown on a display 50.

Figure 12:
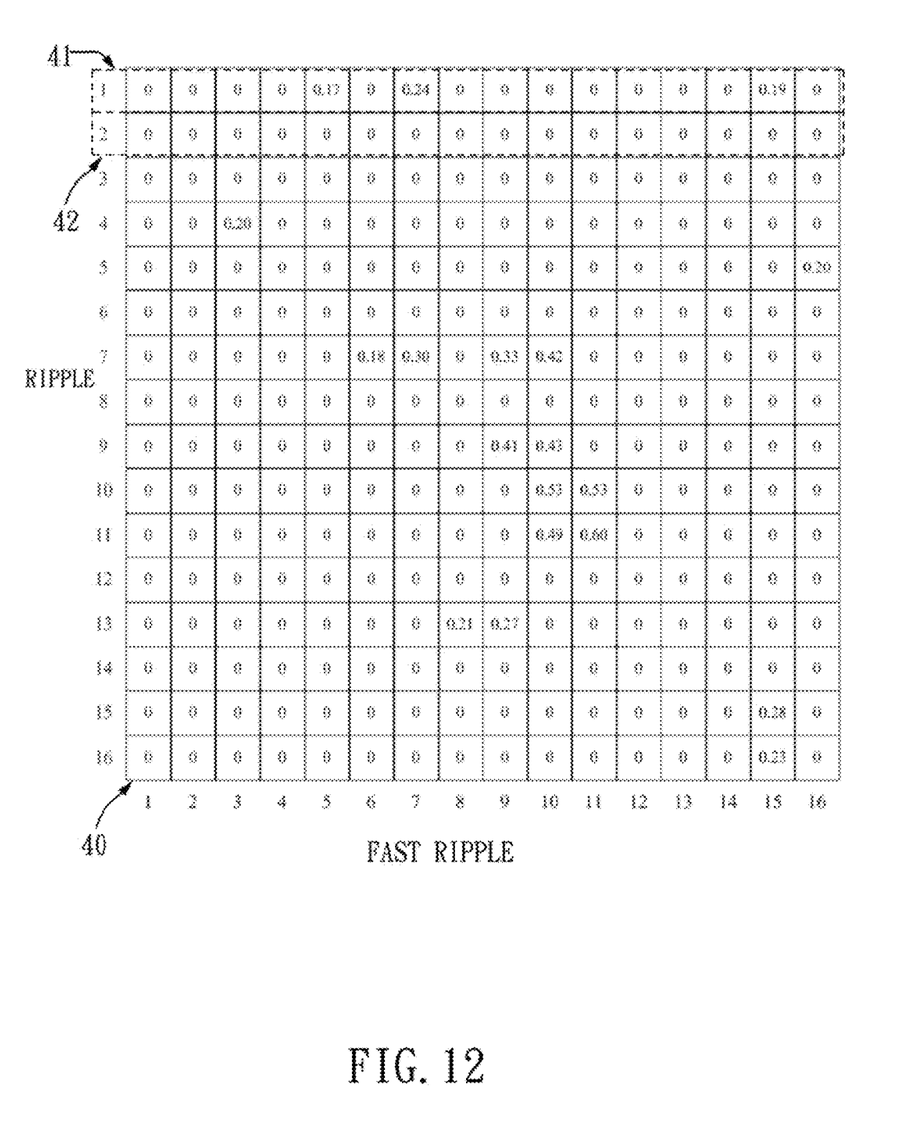
FIG. 12 shows the co-relation table in the second practical application.

Also, as illustrated in FIG. 14, it is another co-relation table 30,40 shown in FIG. 12 after processed and the be illustrated in a display 50.

The advantages and functions of this invention can be summarized as follows.

[1] It utilizes a unique scientific approach to determine the spatial position of seizure onset occurred inside the brain. In this invention, after the electrical voltage difference process, it can significantly reduce the noise or an external inference. After the frequency separating process, the yielding signal or the exciting signal of the nerve cells can be understood.

Also, after a unique co-relation processing procedure, one can obtain a co-relation table which contain numerical information or data. It is extremely scientific and reliable. It is helpful to assist a medical doctor to understand a position where an intracranial brain wave abnormality occurs or started.

[2] the data of the co-relation table can be concretized and visualized. During a selected time segment tx (such as the 141th to 142th second), this invention can generate a co-relation table of the size of (M−1)×(M−1). Also, it can be converted in to different colors or gray scales for different co-relationship. Therefore, it is faster to understand where an intracranial brain wave abnormality occurs or started.

The above embodiments are only used to illustrate the present invention, not intended to limit the scope thereof. Many modifications of the above embodiments can be made without departing from the claims of the present invention.

LIST OF REFERENCE NUMBERS 10 electrode unit
10A electrode collection sub-unit
11 electrodes
20 processing unit
21 original electrical voltage collecting module
22 electrical voltage difference processing module
23 frequency separating processing module
24 electrical voltage wave envelope processing module
25 co-relation processing module
26 visualization processing module
30,40 co-relation table
31,32,41,42 zone
50 display
91 brain portion
T working time
tx time range
B middle zone
W electrical voltage difference wave
W1 first band wave signal
W2 second band wave signal
E1 first band wave envelope signal
E2 second band wave envelope signal
S1 original electrical voltage collecting step
S2 electrical voltage difference processing step
S3 frequency separating processing step
S4 electrical voltage wave envelope processing step
S5 co-relation processing step
S6 visualization processing step

What is claimed is:

1. A system for temporal and spatial detection of seizure onset comprising:
   an electrode unit for positioning inside or on an outer surface of a brain portion, said electrode unit including at least one electrode collection sub-unit, each electrode collection sub-unit containing a plurality of electrodes for corresponding a plurality of detection points, the quantity of the electrodes being defined as M, the quantity of detection points being defined as M as well; and
   a processing unit being electrically connected to said electrode unit and including an original electrical voltage collecting module, an electrical voltage difference processing module, a frequency separating processing module, an electrical voltage wave envelope processing module, and a co-relation processing module;
   said original electrical voltage collecting module being configured to detect said detection points via said electrodes for a working time so as to obtain a plurality of electric voltage variation wave information; wherein the quantity of M being a positive integer and being greater than or equal to 4;
   said electrical voltage difference processing module which connects with said original electrical voltage collecting module being configured to get all the electric voltage variation wave information having the quantity of M and then to compute a subtract operation between two neighboring electrical voltage variation wave information respectively, wherein a plurality of electrical voltage difference waves having the quantity of M−1 are obtained;
   said frequency separating processing module which connects with said electrical voltage difference processing module being configured to conduct a frequency separating process for every electrical voltage difference wave, so that each electrical voltage difference wave being filtered out and separated into a first band wave signal and a second band wave signal, in which said first band wave signal having a frequency range of 80-250 Hz, said second band wave signal having a frequency range of 250-600 Hz;
   said electrical voltage wave envelope processing module which connects with said frequency separating processing module adapted to get a plurality of wave envelope lines of said first band wave signals so as to obtain several first band wave envelope signals and to get a plurality of wave envelope lines of said second band wave signals so as to obtain several second band wave envelope signals; and
   said co-relation processing module which connects with said electrical voltage wave envelope processing module being configured to conduct a co-relation processing during a time segment of said working time and said co-relation processing being performed between respective first band wave envelope signals and second band wave envelope signals, so that a co-relation table in a two-dimensional (M−1) by (M−1) forms, so as to determine a position where an intracranial brain wave abnormality occurs.

2. The system for temporal and spatial detection of seizure onset as claimed in claim 1, wherein said electrode unit being formed as an elongated thin film, a rectangular thin film or a needle structure, or a combination thereof;
   when said electrode unit being the elongated thin film, said electrodes having the quantity of M being aligned, said electrode unit being provided for placing on said outer surface of a brain portion;
   when said electrode unit being said rectangular thin film, said electrode unit containing several rows of electrode collection sub-units that are parallel and connected to each other, said quantity of rows being defined as N, and N being greater than or equal to three so that the electrode unit is a two-dimensional rectangular thin film having at least 4×3 electrodes;
   when said electrode unit being shaped as said needle structure, said electrode unit being provided for inserting into said brain portion.

3. The system for temporal and spatial detection of seizure onset as claimed in claim 1, wherein for each electrode collection sub-unit, every two neighboring electrodes contain a middle zone and said every two neighboring electrodes measure a specific electrical voltage difference wave; and a sampling rate being at least 4 kHz.

4. A method for temporal and spatial detection of seizure onset comprising:

an original electrical voltage collecting step: positioning an electrode unit inside or on an outer surface of a brain portion, said electrode unit including at least one electrode collection sub-unit, each electrode collection sub-unit containing a plurality of electrodes for corresponding a plurality of detection points, the quantity of the electrodes being defined as M, the quantity of detection points being defined as M as well; said electrode unit detecting said detection points via said electrodes for a working time so as to obtain a plurality of electric voltage variation wave information; wherein the quantity of M being a positive integer and being greater than or equal to 4;

an electrical voltage difference processing step: providing a processing unit being electrically connected to said electrode unit, getting all the electric voltage variation wave information having the quantity of M and then computing a subtract operation between two neighboring electrical voltage variation wave information respectively, wherein a plurality of electrical voltage difference waves having the quantity of M−1 are obtained;

a frequency separating processing step: said processing unit conducting a frequency separating process for every electrical voltage difference wave, so that each electrical voltage difference wave being filtered out and separated into a first band wave signal and a second band wave signal, in which said first band wave signal having a frequency range of 80-250 Hz, said second band wave signal having a frequency range of 250-600 Hz;

an electrical voltage wave envelope processing step: said processing unit getting a plurality of wave envelope lines of said first band wave signals so as to obtain several first band wave envelope signals and getting a plurality of wave envelope lines of said second band wave signals so as to obtain several second band wave envelope signals; and a co-relation processing step: said processing unit conducting a co-relation processing during a time segment of said working time about said first band wave envelope signals and said second band wave envelope signals, so as to obtain a co-relation table for determining a position where an intracranial brain wave abnormality occurs.

5. The method for temporal and spatial detection of seizure onset as claimed in claim 4, wherein said electrode unit being formed as an elongated thin film, a rectangular thin film or a needle structure, or a combination thereof;

when said electrode unit being the elongated thin film, said electrodes having the quantity of M being aligned, said electrode unit being provided for placing on said outer surface of a brain portion;

when said electrode unit being said rectangular thin film, said electrode unit containing several rows of electrode collection sub-units that are parallel and connected to each other, said quantity of rows being defined as N, and N being greater than or equal to three so that the electrode unit is a two-dimensional rectangular thin film having at least 4×3 electrodes;

when said electrode unit being shaped as said needle structure, said electrode unit being provided for inserting into said brain portion.

6. The method for temporal and spatial detection of seizure onset as claimed in claim 4, wherein for each electrode collection sub-unit, every two neighboring electrodes contain a middle zone and said every two neighboring electrodes measure a specific electrical voltage difference wave; and a sampling rate being at least 4 kHz.

* * * * *